United States Patent
Yamagata et al.

(10) Patent No.: US 6,482,864 B1
(45) Date of Patent: Nov. 19, 2002

(54) SUSTAINED-RELEASE PREPARATION OF PHYSIOLOGICALLY ACTIVE POLYPEPTIDE AND PRODUCTION THEREOF

(75) Inventors: Yutaka Yamagata, Kobe (JP); Masafumi Misaki, Takarazuka (JP); Susumu Iwasa, Kyotanabe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/319,023

(22) PCT Filed: Mar. 18, 1999

(86) PCT No.: PCT/JP99/01359

§ 371 (c)(1),
(2), (4) Date: May 28, 1999

(87) PCT Pub. No.: WO99/48519

PCT Pub. Date: Sep. 30, 1999

(30) Foreign Application Priority Data

Mar. 20, 1998 (JP) ............................................. 10-071853

(51) Int. Cl.⁷ ...................... A61K 47/32; A61K 38/00; A61K 9/14
(52) U.S. Cl. ........................ 514/772.4; 514/2; 514/964; 424/484; 424/489
(58) Field of Search ........................... 514/772.4, 2, 21, 514/964; 424/85.7, 489, 484, 85.4

(56) References Cited

U.S. PATENT DOCUMENTS

| | | |
|---|---|---|
| 5,478,564 A | 12/1995 | Wantier et al. |
| 5,609,886 A | 3/1997 | Wantier et al. |
| 5,654,010 A | 8/1997 | Johnson et al. |
| 5,667,808 A | 9/1997 | Johnson et al. |
| 6,087,324 A * | 7/2000 | Igari et al. ..................... 514/2 |

FOREIGN PATENT DOCUMENTS

| | | |
|---|---|---|
| EP | 0251476 | 1/1988 |
| EP | 0633020 | 11/1995 |
| EP | 0891774 | 1/1999 |
| WO | WO 90/13285 | 11/1990 |
| WO | WO 91/12882 | 9/1993 |
| WO | WO 94/09898 | 5/1994 |
| WO | WO 94/12158 | 6/1994 |
| WO | 97/01331 * | 1/1997 |
| WO | WO 9735563 | 10/1997 |
| WO | WO 98/27980 | 7/1998 |
| ZA | 912239 | 3/1991 |

OTHER PUBLICATIONS

R. Jeyanthi et al., "Effect of processing parameters on the properties of peptide–containing PLGA microspheres" J. Microencapsulation, 14(2),Mar.–Apr. 1997, pp. 163–174.

Overcashier et al., "Preparation of Excipient–free Recombinant Human Tissue–Type Plasminogen Activator by . . ." Journal of Pharmaceutical Sciences, vol. 86, No. 4, pp. 455–459 (1997).*

* cited by examiner

Primary Examiner—Thurman K. Page
Assistant Examiner—Blessing Fubara
(74) Attorney, Agent, or Firm—Mark Chao; Elaine M. Ramesh

(57) ABSTRACT

A method for producing a sustained-release preparation, which comprises dispersing a physiologically active polypeptide into an organic solvent solution of a biodegradable polymer and removing the organic solvent, wherein the polypeptide is a powder obtained by lyophilizing an aqueous solution of the polypeptide which solution has a water-miscible organic solvent and/or a volatile salt; which improves the ease of handling of the physiologically active polypeptide powder in the process for producing the preparation; which makes it possible to industrially produce the sustained-release preparation in large scale; which provides a sustained-release preparation showing high and stable concentration of the active component in blood in long term, low initial release ratio of the physiologically active polypeptide, and high entrapment ratio of the polypeptide into the sustained-release preparation.

22 Claims, 2 Drawing Sheets

SUSTAINED-RELEASE PREPARATION OF PHYSIOLOGICALLY ACTIVE POLYPEPTIDE AND PRODUCTION THEREOF

This Application is the National Stage of International Application Serial No. PCT/JP99/01359, filed Mar. 18, 1999.

TECHNICAL FIELD

The present invention relates to a sustained-release preparation comprising a physiologically active polypeptide and a method for production thereof.

BACKGROUND ART

It is known that physiologically active polypeptides or their derivatives exhibit a variety of pharmacological activities in vivo. Some of these have been produced on a large scale by utilizing *Escherichia coli,* yeasts, animal cells or host animals such as goat and hamsters due to developed genetic engineering and cell technology, and put to medicinal use. However, these physiologically active polypeptides must be frequently administered because of the generally short biological half-life. The repeated injection put a significant physical burden on patients.

For instance, growth hormone (hereafter sometimes referred to as GH), a representative hormone which is originally produced and secreted in the anterior portion of the pituitary gland, is a physiologically active polypeptide having widely diverse physiological activities such as promotion of growth in the body, metabolism of glucose and lipids, anabolism of protein, and cell proliferation and differentiation. And GH has been recently produced on a large scale by utilizing *Escherichia coli* in genetic recombination technology field, and put to medicinal use clinically and worldwidely. However, GH must be frequently administered in order to maintain an effective blood concentration because of the short biological half-life. Especially, in the case of pituitary dwarfism, a daily subcutaneous administration to infants or young patients over a long period of time ranging from a few months to 10,years or more is the practical administration.

JP-A 3055/1996 (EP-A 633020) discloses a method for producing a sustained-release preparation which comprises permitting a water-soluble polypeptide to permeate into a biodegradable matrix comprising a biodegradable polymer and a metal salt of a fatty acid in an aqueous solution, and sustained-release microcapsules prepared by this method.

JP-A 217691/1996 (WO96/07399) discloses the production of a water-insoluble or slightly water-soluble polyvalent metal salt by using a water-soluble peptide type of physiologically active substance and an aqueous solution of zinc chloride, etc., and a method of producing a sustained-release preparation containing this salt and a biodegradable polymer.

WO 94/12158 discloses addition of a polymer erosion rate modulating agent such as zinc hydroxide in an amount of 0.1 to 30% (w/w) relative to the polymer into a polymer solution, as a method for producing a sustained-release preparation comprising human GH (hereafter sometimes referred to as hGH) and biodegradable polymer. This publication further discloses a method for producing microcapsules as porous particles by spraying an organic solvent solution of hGH and a polymer into liquid nitrogen, with biological activity retained.

WO 92/17200and Nature Medicine, Vol. 2, p. 795 (1996) disclose a method for producing a sustained-release preparation by using a zinc salt of human GH.

WO 95/29664 discloses a method for producing sustained-release microcapsules which comprises the steps of dispersing a metal salt such as zinc carbonate in a solid state into a polymer solution, adding a physiologically active substance (hormone, etc.), and dispersing the physiologically active substance and a metal cation component separately into a biodegradable polymer.

Although, as described above, various attempts have been made to produce a sustained-release preparation while retaining the physiological activity of a physiologically active polypeptide, a clinically satisfactory preparation has not been obtained yet since some physiologically active polypeptides have problems such as a low entrapment ratio of the physiologically active polypeptide in the preparation, an excess release at an initial stage after administration, an unattained constant release over a long period of time, or an unretained satisfactory blood concentration over a long period of time. Further, production methods, in many cases, are not suitable for industrialization which premises a large-scale production in the present situation.

In a method for producing a sustained-release preparation by using what is called a S/O emulsion which is obtained by adding and dispersing the physiologically active polypeptide powder (solid phase: hereafter sometimes referred as an S phase) discretely into an organic solvent in which is dissolved a polymer (O phase), it is possible to entrap the physiologically active polypeptide in relatively stable manner. However, it is necessary that a large quantity of the physiologically active polypeptide is efficiently handled as a solid. Furthermore, there are many problems in the process for producing the sustained release preparation, such as controlling of the particle size of the powder in the S/O dispersion which is essential, because the particle size influences greatly the quality of the obtained sustained-release preparation.

Therefore, it is desired to have a method for producing the sustained-release preparation by which it is possible to produce the sustained-release preparation with stable quality in high yield in large scale in addition to satisfying any problem such as maintaining the stability of the physiologically active polypeptide, the preparation of powder which is superior in handling the atomization of the powder in the process for producing the preparation.

DISCLOSURE OF THE INVENTION

The present inventors studied to solve the above problems, and unexpectedly, first discovered the physiologically active polypeptide powder which has a small particle size in addition to which is superior for handling in the process for producing the preparation, while the physiological activity of the, polypeptide is maintained, is achieved where a water-miscible organic solvent and/or a volatile salt is/are added into the aqueous solution of the physiologically active polypeptide, and then the resultant solution is lyophilized. Furthermore, the present inventors found out unexpectedly the fact that the entrapment ratio and the sustained-release effect of the preparation are improved where the physiologically active polypeptide powder obtained as mentioned above is dispersed, into a solution of a biodegradable polymer dissolved into an organic solvent, and then the organic solvent is removed to produce the sustained-release preparation. As mentioned above, the present inventors accomplished the present invention.

The present invention is concerned with (1) A method for producing a sustained-release preparation, which comprises dispersing a physiologically active polypeptide into an organic solvent solution of a biodegradable polymer and removing the organic solvent: wherein the polypeptide is a powder obtained by lyophilizing an aqueous solution of the polypeptide which solution has a water-miscible organic solvent and/or a volatile salt;

(2) the method according to the above (1), wherein the average particle size of the powder is not more than 10 μm;

(3) the method according to the above (1), wherein the physiologically active polypeptide is growth hormone;

(4) the method according to the above (3), wherein the growth hormone is human growth hormone:

(5) the method according to the above (1), wherein the water-miscible organic solvent is alcohol;

(6) the method according to the above (5), wherein the alcohol is methanol or ethanol;

(7) the method according to the above (5), wherein the alcohol is ethanol;

(8) the method according to the above (1), wherein the volatile salt is an ammonium salt;

(9) the method according to the above (8), wherein the ammonium salt is ammonium acetate, ammonium bicarbonate or ammonium carbonate;

(10) the method according to the above (8), wherein the ammonium salt is ammonium acetate;

(11) the method according to the above (5), wherein a final concentration of the alcohol to be added to the aqueous solution of the physiologically active polypeptide is 0.03 to 0.5% (V/V);

(12) the method according to the above (8), wherein the molar ratio of the ammonium salt relative to the physiologically active polypeptide is 10 to 80;

(13) the method according to the above (1), wherein the biodegradable polymer is lactic acid/glycolic acid polymer;

(14) the method according to the above (13), wherein the molar ratio of the lactic acid/glycolic acid of lactic acid/glycolic acid polymer is 100/0 to 40/60;

(15) the method according to the above (13), wherein the weight-average molecular weight of the lactic acid/glycolic acid polymer is 3,000 to 50,000;

(16) the method according to the above (13), wherein the lactic acid/glycolic acid polymer is in a form of a polyvalent metal salt;

(17) the method according to the above (16), wherein the polyvalent metal is zinc;

(18) the method according to the above (1), wherein the sustained-release preparation is a microcapsule;

(19) the method according to the above (18), wherein the average particle size of the microcapsule is 0.1 μm to 300 μm;

(20) the method according to the above (1), wherein the sustained-release preparation is for injection;

(21) a sustained-release preparation produced by the method according to the above (1);

(22) a method for producing a physiologically active polypeptide powder which comprises adding (i) a water-miscible organic solvent and/or (ii) a volatile salt into an aqueous solution of a physiologically active polypeptide and lyophilizing the resulting solution;

(23) a physiologically active polypeptide powder which is obtained by the method according to the above (22);

(24) the physiologically active polypeptide powder according to the above (23), wherein the average particle size of the powder is not more than 10 μm;

(25) use of the physiologically active polypeptide powder according to the above (23), for the manufacture of a medicament;

(26) use of (i) a water-miscible organic solvent and/or (ii) a volatile salt for producing a physiologically active polypeptide powder which has a small particle size;

(27) use of (i) a water-miscible organic solvent and/or (ii) a volatile salt according to the above (26), wherein the particle size is not more than 10 μm;

(28) a sustained-release preparation which is obtainable by the method as described in the above (1);

(29) a sustained-release preparation containing a physiologically active polypeptide and a polyvalent metal salt of a biodegradable polymer, wherein the initial release ratio is not more than 40%;

(30) the sustained-release preparation according to the above (29), wherein the physiologically active polypeptide is in a form of powder having, the average particle size of not more than 10 μm;

(31) the sustained-release preparation according to the above (29), wherein the physiologically active polypeptide is growth hormone;

(32) the sustained-release preparation according to the above (29), wherein the biodegradable polymer is a lactic acid/glycolic acid polymer;

(33) the sustained-release preparation according to the above (29), wherein the sustained-release preparation is microcapsule;

(34) the sustained-release preparation according to the above (33), wherein the average particle size of the microcapsule is 0.1 to 300 μm;

(35) the sustained-release preparation according to the above (29), which can effectively release a physiologically active polypeptide for a period ranging from one week to one month; and (36) the sustained-release preparation according to the above (29), which contains 0.1% to 30% (W/W) of the physiologically active polypeptide.

Examples of the biodegradable polymers used in the present invention include polymers synthesized from one or more α-hydroxycarboxylic acids (e.g., glycolic acid, lactic acid, etc.), hydroxydicarboxylic acids (e.g., malic acid, etc.), hydroxytricarboxylic acids (e.g., citric acid, etc.) etc., by catalystfree dehydration condensation polymerization and having a free carboxyl group(s), mixtures thereof, poly-α-cyanoacrylic esters, polyamino acids (e.g., poly-γ-benzyl-L-glutamic acid, etc.) and maleic anhydride copolymers (e.g., styrene/maleic acid copolymers, etc.). The polymers may be homopolymers or copolymers. Polymerization may be of the random, block or graft type. When the above-mentioned α-hydroxycarboxylic acids, hydroxydicarboxylic acids and hydroxytricarboxylic acids have an optical active center in their molecular structures, they may be of the D-, L- or DL-configuration.

Among these polymers, a biodegradable polymer having a free terminal carboxyl group such as polymers synthesized from α-hydroxycarboxylic acids (e.g., glycolic acid, lactic acid, etc.) (e.g., lactic acid/glycolic acid copolymer, polylactic acid, etc.) and poly- α-cyanoacrylic acid esters are preferred.

The biodegradable polymer is more preferably a polymer synthesized from α-hydroxycarboxylic acids, etc., especially preferably lactic acid/glycolic acid copolymer, etc.

In the present specification, lactic acid/glycolic acid copolymer as well as homopolymers such as polylactic acid and polyglycolic acid are sometimes simply referred to as lactic acid/glycolic acid polymer.

When the biodegradable polymer used is a lactic acid/glycolic acid polymer (a lactic acid/glycolic acid copolymer or homopolymer), its composition ratio (mol %) is preferably about 100/0 to about 40/60, more preferably about 85/15 to about 50/50.

The weight-average molecular weight of the above-described lactic acid/glycolic acid polymer is preferably about 3,000 to about 50,000, more preferably about 3,000 to about 25,000, further more preferably about 5,000 to about 20,000.

The degree of dispersion (weight-average molecular weight/number-average molecular weight) of the lactic acid/glycolic acid polymer is preferably about 1.2 to about 4.0, more preferably about 1.5 to about 3.5.

Regarding weight -average molecular weight and degree of dispersion, the present specification holds that the former is in terms of polystyrene as determined by gel permeation chromatography (GPC) using 9 polystyrenes as reference substances with weight-average molecular weights of 120,000, 52,000, 22,000, 9,200, 5,050, 2,950, 1,050, 580 and, 162, respectively, and that the latter is calculated therefrom. The above determination is carried out using a GPC column KF804L×2 (produced by Showa Denko, Japan) and an RI monitor L-3300 (produced by Hitachi, Ltd., Japan) with chloroform as a mobile phase.

A biodegradable polymer having a free terminal carboxyl group(s) is a biodegradable polymer wherein the number-average molecular weight based on GPC measurement and the number-average molecular weight based on terminal group quantitation almost agree with each other. The number-average molecular weight based on terminal group quantitation is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide while stirring at room temperature (20° C.) with phenolphthalein as an indicator to determine the carboxyl group content; the number-average molecular weight based on terminal group quantitation is calculated from the following equation:

Number-average molecular weight based on terminal group quantitation=$20000 \times A/B$ A : Weight mass (g) of biodegradable polymer
B: Amount (ml) of the 0.05 N alcoholic solution of potassium hydroxide added until titration end point is reached While the number-average molecular weight based on terminal group quantitation is an absolute value, that based on GPC measurement is a relative value that varies depending on various analytical conditions (e.g., kind of mobile phase, kind of column, reference substance, slice width chosen, baseline chosen etc.); it is therefore difficult to have an absolute numerical representation of these two values. However, the description that the number-average molecular weight based on GPC measurement and that based on terminal group quantitation almost agree means, for instance, that the number-average molecular weight based on terminal group quantitation falls within the range from about 0.5 to about 2 times, preferably from about 0.7 to about 1.5 times, of the number-average molecular weight based on GPC measurement in a polymer which is synthesized from one or more α-hydroxycarboxylic acids.

For example, in the case of a polymer having a free terminal carboxyl group(s) and which is synthesized from one or more α-hydroxycarboxylic acids by catalyst-free dehydration condensation polymerization, the number-average molecular weight based on GPC measurement and the number-average molecular weight based on terminal group quantitation almost agree with each other. On the other hand, in the case of a polymer having substantially no free terminal carboxyl groups and which is synthesized from a cyclic dimer by ring-opening polymerization using a catalyst, the number-average molecular weight based on terminal group quantitation is significantly (about 2 times or more) higher than that based on GPC measurement. This difference makes it possible to clearly differentiate a polymer having a free terminal carboxyl group(s) from a polymer having no free terminal carboxyl group.

A lactic acid/glycolic acid polymer having a free terminal carboxyl group(s) can be produced by a per se known process such as that described in JP-A 28521/1986 (e.g., process by catalyst-free dehydration condensation polymerization reaction or dehydration condensation polymerization reaction in the presence of an inorganic solid acid catalyst).

The decomposition/elimination rate of a lactic acid/glycolic acid polymer varies widely, depending on composition rate or weight-average molecular weight. A physiologically active polypeptide release duration can be extended (e.g., to about 6 months) by lowering the glycolic acid ratio or increasing the molecular weight, since decomposition/elimination is usually delayed as the glycolic acid ratio decreases. Conversely, drug release duration can be shortened (e.g., to about one week) by increasing the glycolic acid ratio or decreasing the molecular weight. To obtain a sustained-release preparation which can effectively release a physiologically active polypeptide for a period ranging from one week to two months, it is preferable to use a lactic acid/glycolic acid polymer whose composition ratio and weight-average molecular weight are within the above-described ranges.'

Therefore the composition of a biodegradable polymer used in the present invention is preferably selected according to the desired kinds of a physiologically active polypeptide and the desired duration. In a specific example, for instance, when GH is used as a physiologically active polypeptide, the biodegradable polymer is preferably lactic acid/glycolic acid polymer, more preferably lactic acid/glycolic acid copolymer. In the lactic acid/glycolic acid copolymer, lactic acid/glycolic acid composition ratio (mol %) is preferably about 85/15 to about 50/50, more preferably about 75/25 to about 50/50. The weight-average molecular weight of the lactic acid/glycolic acid copolymer is preferably about 8,000 to about 20,000, more preferably about 10,000 to about 20,000. Further, the degree of dispersion (weight-average molecular weight/number-average molecular weight) of the lactic acid/glycolic acid polymer is about 1.2 to about 4.0, more preferably about 1.5 to about 3.5.

The lactic acid/glycolic acid polymer used can be produced by the known methods such as those described in the above publication and the like. The polymer is preferably one that is produced by catalyst-free dehydration condensation polymerization. It is preferable that the lactic acid/glycolic acid polymer (PLGA) wherein the number-average molecular weight based on terminal group quantitation and the number-average molecular weight based on GPC measurement almost agree with each other is used.

Further, two kinds of lactic acid/glycolic acid polymers differing in composition ratio and/or weight-average molecular weight may be used in an admixture of given ratio. The typical example is a mixture of lactic acid/glycolic acid polymer wherein the composition ratio of lactic acid/glycolic acid (mol %) is about 75/25 and the weight-average molecular weight is about 10,000 and lactic acid/glycolic acid copolymer wherein the composition ratio of lactic acid/glycolic acid (mol %) is about 50/50 and the weight-average molecular weight is about 12,000. The preferred weight ratio of these copolymers of the mixture is about 25/75 to about 75/25, respectively.

The biodegradable polymer used in the present invention can be metal salts of the above mentioned biodegradable polymer. For example, various polyvalent metal salts of the biodegradable polymer and the like described in WO97/01331 can be used. Preferably, polyvalent metal salt of the lactic acid/glycolic acid polymer, etc., (more preferably, zinc salt, calcium salt, magnesium salt, etc., further more preferably zinc salt, etc.) can be used. The metal of the polyvalent metal salt used in this invention is not particularly limited as long as it does not cause any adverse effect to a living body. It is exemplified by polyvalent metals such as bivalent salts (e.g., Fe:, Zn, Cu, Ca, Mg, Al, Sn, Mn, etc.), trivalent salts (e.g., Fe, Al, Mn, etc.), tetravalent salts (e.g., Sn, etc.) and the like.

In the present specification, the biodegradable polymer is sometimes referred as the biodegradable polymer in case that it is the metal salt thereof. For example, also lactic acid/glycolic acid polymer is sometimes referred as lactic acid/glycolic acid polymer in the case that it is the polyvalent metal salt thereof.

The above polyvalent metal salt of the biodegradable polymer can be produced by the method described in WO97/01331 or similar methods.

In case that polyvalent metal salt of the biodegradable polymer is the salt of zinc, it can be produced by reaction of the biodegradable polymer and zinc oxide in an organic solvent.

In the above method, at first the organic solvent solution of the biodegradable polymer-zinc oxide complex is prepared by coexistence of biodegradable polymer and zinc oxide in the organic solvent. In that case, although the concentration of the biodegradable polymer in the solvent is depending on molecular weight thereof or the kind of the organic solvent, etc., for example, the concentration is about 0.1 to about 80% (W/W), preferably about 1 to about 70% (W/W), more preferably about 2 to about 60% (W/W). Although the amount of the added zinc oxide is different depending on the kind of the organic solvent, for example, the amount is about 0.001 to about 2% (W/W), preferably about 0.01 to about 1.5% (W/W), more preferably about 0.1 to about 1% (W/W), based on the amount of the biodegradable polymer, as described in JP-A 231252/1998.

Concerning the order in which to add the biodegradable polymer and zinc oxide into the organic solvent, zinc oxide in powder form or suspended in the organic.solvent can be added into the solution prepared by dissolved the biodegradable polymer into organic solvent, or on the contrary, the organic solvent solution of the biodegradable polymer can be added into the suspension prepared by suspending zinc oxide into the organic solvent. Both of the biodegradable polymer and zinc oxide can be mixed in powder form, then the organic solvent can be added.

The physiologically active polypeptide used in the present invention includes a physiologically active polypeptide having molecular weight of preferably about 1,000 to about 50,000, more preferably about 5,000 to about 40,000.

The representative activity of the physiologically active polypeptide is hormonal activity. The physiologically active polypeptide can be natural products, synthetic products, semi-synthetic products, and their derivatives and analogues. The mode of action of the physiologically active polypeptide can be agonistic or antagonistic.

The physiologically active polypeptide for use in the present invention includes peptide hormones, cytokines, peptide neurotransmitters, hematopoietic factors, various growth factors, enzymes, polypeptide antibiotics and analgesic peptides, etc.

Examples of the peptide hormones include insulin, somatostatin, somatostatin derivative (Sandostatin; see U.S. Pat. Nos. 4,087,390, 4,093,574, 4,100,117 and 4,253,998), growth hormones (GH), sodium diuretic peptides, gastrin, prolactin, adrenocorticotropic hormone (ACTH), ACTH derivatives (e.g., ebiratide), melanocyte-stimulating hormone (MSH), thyrotropin-releasing hormone (TRH) and salts and derivatives thereof (see JP-A 121273/1975 and 116465/1977), thyroid-stimulating hormone (TSH), luteinizing hormone (LH), follicle-stimulating hormone (FSH), human chorionic gonadotropin (HCG), thymosin, motilin, vasopressin, vasopressin derivative [desmopressin, see Folia Endocrinologica Japonica, Vol. 54, No. 5, pp. 676–691 (1978)], oxytocin, calcitonin, parathyroid hormone (PTH), glucagon, secretin, pancreozymin, cholecystokinin, angiotensin, and human placental lactogen, etc. The peptide hormones are preferably insulin and growth hormones, etc.

The cytokines include lymphokines and monokines, etc. The lymphokines include, for example, interferons (alpha, beta and gamma) and interleukins (IL-2, 3, 4, 5, 6, 7, 8, 9, 10, 11, 12), etc. The monokines include, for example, interleukin-1 (IL-1), and tumor necrosis factor (TNF), etc. The preferred cytokine is a lymphokine, etc., more preferred is interferon, etc., a particularly preferred one is interferon-α.

The peptide neurotransmitters include substance P, serotonin and GABA, etc.

The hematopoietic factors include erythropoietin (EPO), colony stimulating factors (G-CSF, GM-CSF, M-CSF, etc.), thrombopoietin (TPO), platelet-derived growth factor, and megakaryocyte potentiator, etc.

The various growth factors include, for example, basic and acidic fibroblast growth factors (FGF) and their families (e.g.,EGF, TGF-α, TGF-β,PDGF, acidic FGF, basic FGF, FGF-9, etc.), nerve growth factor (NGF) and its family (e.g., BDNF, NT-3, NT-4, CNTF, GDNF, etc.), insulin-like growth factors (e.g. IGF-1, IGF-2, etc.) and bone morphogenetic protein (BMP) and its family, etc.

The enzymes include, for example, superoxide dismutase (SOD), urokinase, tissue plasminogen activator (TPA), asparaginase and kallikrein, etc.

The polypeptide antibiotics include, for example, polymixin B, colistin, gramicidin and bacitracin, etc.

The analgesic peptides include for example, enkephalin, enkephalin derivatives (see U.S. Pat. No. 4,277,394 and EP-A 31567), endorphin, and kyotorphin, etc.

Further, the physiologically active polypeptides include thymopoietin, dynorphin, bombesin, caerulein, thymostimulin, thymic humoral factor (THF), blood thymic factor (FTS) and derivatives thereof (see U.S. Pat. No. 4,229,438), other thymic factors [Igaku no Ayumi, Vol.125, No. 10, pp. 835–843 (1983)], neurotensin, bradykinin, and endothelin-antagonistic peptides (see EP-A 436189, 457195 and 496452, and JP-A 94692/1991 and 130299/1991), etc.

The particularly preferred physiologically active polypeptides include growth hormone and insulin, etc., further particularly preferred is growth hormone (especially human growth hormone).

In the present invention, when the physiologically active polypeptide contains a metal, the content of the metal is preferably not greater than 0.1% (W/W), more preferably not greater than 0.01% (W/W), and most preferably not greater than 0.001% (W/W). Thus, substantially metal-free physiologically active polypeptides are most suited for the present invention. Crystalline insulin, for example, usually contains small amounts of heavy metals such as zinc, nickel, cobalt and cadmium, etc. Insulin containing 0.4% (W/W) zinc exists as a stable hexamer and appears to be relatively inert in the interaction with the metal salt of biodegradable polymer.

If necessary, the metals occurring in the physiologically active polypeptide can be previously removed. As the method of removing the metals, known methods are employed. For example, dialyzing an acidic aqueous hydrochloric acid solution of insulin against water or an aqueous solution of ammonium acetate and lyophilizing the dialysate can provide amorphous insulin with minimal metal content.

Growth hormone originating from any species can be used, and is preferably human growth hormone. Further, although natural products extracted from the pituitary gland can be used for the present invention, genetic recombinant typeGH (see JP-B 12996/1994, JP-B-48987/1994) is preferred. The recombinant type hGH having the same structure as a natural type without methionine at the N-terminal group is more preferred. Such GH may be in the form of a metal salt, and one containing substantially no metal is also used. The 20K dalton type of hGH (see JP-A 101877/1995, JP-A 265404/1998) as well as the 22K dalton type of hGH can be used. Furthermore, the derivatives or analogues of hGH (see WO99/03887) can be used.

As the physiologically active polypeptide, can be used an extract-or a purified substance from an organism, a substance synthesized chemically, a production by the method of biotechnology or the like and can be one produced by the above method. In order to synthesize the product having high purity in large scale, the adoption of biotechnology is preferred. In any case that the above method is adopted, it is need that the physiological active polypeptide is purged or purified from the crude preparations such as tissues, body fluids, synthetic substances, or recombinant cells or recombinant fungi. In that case, a well known method to isolate and purify the peptide or the protein can be adopted ("Protein" written by Kazuo SATAKE published by Asakura Syoten; "Physiologically Active Peptide" which is a pharmacia review, No. 3, published by the Pharmaceutical Society of Japan). In particular, by combining some liquid chromatographies ("High-speed Liquid Chromatography of Protein or Peptide" edited by Nobuo UI et al. published by Kagakudojin), it is possible to obtain the physiologically active polypeptide having high purity in high yield without a loss of the physiological activity. If necessary, the step of desalting can be preferably adopted as the final step of the process for purification. The concentration of the physiologically active polypeptide in the aqueous solution is, for example, 0.01% (W/V) to 30% (W/V), preferably 0.03% (W/V) to 10% (W/V), more preferably 0.05% (W/V) to 3% (W/V), etc., however it is not particularly limited thereto. When the physiologically active polypeptide is hGH, the concentration of hGH in the aqueous solution is preferably 0.01% (W/V) to 5% (W/V), more preferably 0.05% (W/V) to 0.5% (W/V).

In the present invention, the water-miscible organic solvent, which can be added into the solution of the physiologically active polypeptide, is, for example, alcohol (e.g. methanol, ethanol, isopropanol, etc., preferably methanol, ethanol, etc.), acetone, etc. The above organic solvent can be used in admixture thereof having a suitable mixing ratio. Preferable organic solvent is alcohol, more preferable one is ethanol, alone. The added amount (concentration) of the water-miscible organic solvent is about 0.03 to 0.5% (V/V), preferably about 0.06 to 0.25% (V/V); more preferably about 0.1 to 0.15% (V/V), by volume-ratio. By lyophilizing the resulting aqueous solution of physiologically active polypeptide obtained by adding the water-miscible organic solvent, it is possible to prepare the physiologically active polypeptide powder which is easy of handling (superior handling) and is very fine (has a small particle size).

As a volatile salt, which can be added into the aqueous solution of the physiologically active polypeptide, in the present invention is, for example, ammonium salt (e.g., ammonium acetate, ammonium bicarbonate, ammonium carbonate, ammonium chloride, etc., preferably ammonium acetate, etc.). The volatile salt can be used in admixture thereof in a given ratio. The added amount of the volatile salt relative to the aqueous solution of the physiologically active polypeptide is about 10 times to about 80 times mole, preferably about 10 times to about 70 times mole, more preferably about 15 times to about 70 times mole, further more preferably about 20 times to about 70 times mole, most preferably about 20 times to about 50 times mole by mole ratio. Similar to that the water-miscible organic solvent is added, by lyophilizing the resulting aqueous solution of the physiologically active polypeptide obtained by adding the volatile salt, it is possible to prepare the physiologically active polypeptide powder which is easy of handling (superior handling) and is very fine (has a small particle size).

In the present invention, the water-miscible organic solvent and/or the volatile salt added into the aqueous solution of the physiologically active polypeptide can be singly used or in admixture thereof. When the water-miscible organic solvent and the volatile salt are used in admixture thereof, they can be added into the aqueous solution of the physiologically active polypeptide in accordance with the above amount respectively.

When the aqueous solution of the physiologically active polypeptide including the water-miscible organic solvent and/or the volatile salt obtained by the above method is subjected to as the lyophilization, the lyophilization method can be adopted any method used in any field such as the any field concerned with water as well as fields of pharmaceuticals or foods ("Development of Drugs" Vol. 11 edited by Yoshinobu NAKAI published by Hirokawa Syoten). For example, the aqueous solution of the physiologically active polypeptide is filled in a vial or an ampule, etc., and then the aqueous solution is subjected to the process for drying after freezing. In that case, though the sample can be put in the drier after the freezing out of the apparatus, in general, preferably the sample is frozen in the suitable temperature control in the apparatus. The process for drying can be performed gradually. The recent lyophilization apparatus is capable of the temperature control or the vacuum control, and is capable of the selection of the optimum condition for the subjected physiologically active polypeptide. The concentration of the physiologically active polypeptide which is subjected to the process for lyophilization is, for example, 0.1% (W/V) to30% (W/V), preferably 0.03% (W/V) to 10% (W/V), more preferably 0.05% (W/V) to 3% (W/V) and the like in the aqueous solution, but it is not particularly limited thereto. When the physiologically active polypeptide is hGH, the concentration of hGH in the aqueous solution is preferably 0.01% (W/V) to 5% (W/V), more preferably 0.05% (W/V) to 0.5% (W/V).

The organic solvent used in the present invention preferably has a boiling point not exceeding 120° C. Such organic solvent includes halogenated hydrocarbons (e.g., dichloromethane, chloroform, carbon tetrachloride, etc.), alcohols (e.g.,. ethanol, methanol, 1,4-butanediol, 1,5-pentanediol, etc.), ethyl acetate, acetonitrile, and so on.

These solvents. can also be used as a mixture in a given ratio. The preferred organic solvent used singly includes, for instance, dichloromethane and acetonitrile, etc. The preferred organic solvent used as a mixture includes, for example, combination of halogenated hydrocarbons (e.g., dichloromethane, chloroform, etc.) and alcohols (e.g., ethanol, methanol, 1,4-butanediol, 1,5-pentanediol) or acetonitrile. Especially, combination of dichloromethane and acetonitrile is used widely. The mixing ratio (volume ratio) of halogenated hydrocarbons relative to alcohols or acetonitrile ranges from about 40:1 to about 1:1, preferably from about 20:1 to about 1:1. In particular, it is preferred that hydrocarbon halide (e.g., dichloromethane, etc.) is singly used, or a solvent mix consisting essentially of hydrocarbon halide and acetonitrile at mixing ratio of 9:1 to 1:1 is used. The concentration of the biodegradable polymer in the solution is different depending on molecular weight, the kind of the organic solvent and so on. For example, it can be about 0.01 to about 80% (W/W), preferably about 0.1 to about 70% (W/W), more preferably about 1 to about 60% (W/W).

The sustained-release preparation in the present invention is produced by removing the organic solvent from the S/O dispersion wherein the physiologically active polypeptide powder (S phase) obtained by lyophilizing the solution of physiologically active polypeptide added to the water-miscible organic solvent and/or the volatile salt therein is dispersed into the solution in what is dissolved the biodegradable polymer into the organic solvent (O phase). The method is, for example, (a) in-water drying method (S/O/W method), (b) phase separation method (Coacervation method) and (c) spray-drying method, or the other methods according to these methods. Below, there is described, for example, the method for producing the microcapsule, as the sustained-release preparation.

(a) In-Water Drying Method (S/O/W Method)

According to this method, at first the water-miscible organic solvent and/or the volatile salt is added into the aqueous solution of the physiologically active polypeptide, and then, the physiologically active polypeptide powder (S phase) is produced by lyophilization. The biodegradable polymer is dissolved in the organic solvent, and then, the above physiologically active polypeptide powder is dispersed into the resulting organic solvent solution. The ratio (ratio by weight) of the physiologically active polypeptide and the biodegradable polymer is, for example, about 1:1000 to about 1:1, preferably about 1:200 to about 1:5, more preferably about 1:100 to about 1:5. Preferably, an external physical energy is added to disperse the physiologically active polypeptide powder uniformly into the organic solvent solution. As the above method, is used, for example, an irradiation of ultrasonic wave, a turbine stirrer, a homogenizer and so on. As to the average particle size of the physiologically active polypeptide in the organic solvent solution, it is preferably not more than about 10 $\mu$m, more preferably about 0.1 to 10 $\mu$m, further more preferably about 0.5 to 5 $\mu$m, and which is easily realized by using the physiologically active polypeptide powder obtained by the method in the present invention. In the present invention, the average particle size of the physiologically active polypeptide means the value obtained by using a laser diffraction particle size analyzer (commercially available under the name of SALD2000A from Shimadzu Corp.) after dispersing the physiologically active polypeptide into the organic solvent such as dichloromethane by using a homogenizer. In this process, the physiologically active polypeptide is added into the organic solvent at the concentration of about 20 to 100 mg/ml, and then dispersed using a homogenizer, such as Polytron (Kinematica) at about 20,000 rpm for about 30 to 60 seconds. The dispersion is diluted adequately with the organic solvent for measuring the average particle size by using a laser diffraction particle size analyzer.

Further, the organic solvent dispersion (S/O dispersion) prepared as above mentioned is added into an aqueous solvent (W phase), and then the same external physical energy as above mentioned, for example, an irradiation of ultrasonic wave, a turbine stirrer, a homogenizer and so on is added to form the S/O/W emulsion. Then, the organic solvent of O phase is evaporated to produce the microcapsule. The volume of the water phase is selected from the numbers generally about 1 times to about 10,000 times, preferably about 2 times to about 5,000 times, more preferably about 5 times to about 2,000 times based on the volume of the O phase.

An emulsifer can be added into the above external water phase. As the emulsifer, can be used any one which is capable of forming the generally stable S/O/W emulsion. As the above emulsifer is, for example, anionic surfactants, nonionic surfactants, derivatives of polyoxyethylene castor oil, polyvinylpyrrolidones, polyvinyl alcohols, carboxymethyl celluloses, lecithin, gelatin, hyaluronic acids, etc. These emulsifiers can be used in admixture thereof in a given ratio. The concentration of the emulsifer in the external water phase is, preferably about 0.001% to 20% (w/w), more preferably about 0.01% to 10% (w/w), particularly preferably about 0.05% to 5% (w/w).

The thus obtained microcapsules are recovered by centrifugation or filtration, washed with distilled water to remove the emulsifier, etc. adhering to the surface of microcapsules, redispersed in distilled water, and lyophilized. Then, if necessary, water and the organic solvent in the microcapsules are further removed by heating. The heating can be conducted under reduced pressure. Regarding the heating conditions, heating and drying are conducted at a temperature not lower than a glass transition temperature of the biodegradable polymer and not so high as to cause aggregation of each microcapsule particle. The heating and drying are conducted preferably at a temperature ranging from the glass transition temperature of the biodegradable polymer to a temperature which is about 30° C. higher than the glass transition temperature. The glass transition temperature is defined as the intermediate glass transition point obtained using a differential scanning calorimeter when the temperature is increased at a rate of 10 to 20° C. per minute.

(b) Phase Separation Method (Coacervation Method)

When microcapsules are produced by the present method, a coacervating agent is gradually added to the S/O dispersion described as the above (a) under stirring to precipitate and solidify microcapsules. The amount of the coacervating agent used is about 0.01 to about 1,000 times by volume, preferably about 0.05 to about 500 times by volume, especially preferably about 0.1 to about 200 times by volume. Any coacervating agent can be used, as long as it is a polymeric, mineral oil or vegetable oil compound miscible with the organic solvent for dissolution of a biodegradable polymer and it does not dissolve the biodegradable polymer used. Specifically, examples of such coacervating agents include silicone oil, sesame oil, soybean oil, corn oil, cottonseed oil, coconut oil, linseed oil, mineral oil, n-hexane and n-heptane, etc. Two or more of these can be used in combination. The thus obtained microcapsules are recovered by filtration, washed repeatedly with heptane, etc. to remove the coacervating agent. Further, washing is conducted in the same manner as in the above (a), followed by lyophilization.

In the production of microcapsules by the in-water drying method or coacervation method, an antiaggregation agent can be added for preventing aggregation of particles. Examples of the antiaggregation agent can be used, for instance, water-soluble polysaccharides such as mannitol, lactose, glucose, starches (e.g., corn starch, etc.), hyaluronic acid and its alakaline metal salt; protein such as glycine, fibrin and collagen; and inorganic salts such as sodium chloride and sodium hydrogen phosphate, etc.

(c) Spray-Drying Method

When microcapsules are produced by the present method, the S/O dispersion described as above (a) is sprayed via a nozzle into the drying chamber of a spray drier to volatilize the organic solvent in the fine droplets in a very short time to produce microcapsules. Such nozzles include, for instance, a two-fluid nozzle type, a pressure nozzle type and a rotary disc type, etc. It is also advantageous, if necessary, to spray an aqueous solution of the above-described antiaggregation agent via another nozzle in order to prevent aggregation of each microcapsule particle. The thus obtained microcapsules are washed in the same manner as in the above (a), if necessary followed by heating (if necessary under reduced pressure) to remove water and the organic solvent.

The sustained-release preparation in the present invention is preferably in the condition of the microparticle, because the sustained-release preparation is applied through the needle for injection which is generally used for subcutaneous injection or intramuscular injection, for fear the patient should feel excessive pain. The particle size of the sustained-release preparation is, for example, about 0.1 to 300 $\mu$m preferably about 1 to 150 $\mu$m, more preferably about 2 to 100 $\mu$m as the average particle size.

The amount of the physiologically active polypeptide included in the sustained-release preparation in the present invention is, for example, about 0.1 to 30% (W/W), preferably about 0.2 to 20% (W/W), more preferably about 0.5 to 10% (W/W). The average particle size of the physiologically active polypeptide is preferably not more than about 10 $\mu$m, more preferably about 0.1 to 10 $\mu$m, further more preferably about 0.5 to 5 $\mu$m.

The amount of the biodegradable polymer included in the sustained-release preparation in the present invention is, for example, about 30 to 99.9% (W/W), preferably about 60 to 97% (W/W), more preferably about 70 to 90% (W/W).

The initial release ratio of physiologically active polypeptide from the sustained-release preparation is preferably not more than about 40%, more preferably about 1 to 40%, further more preferably about 3 to 35%. The initial release ratio means that for one day (24 hours) after subcutaneous administration. This ratio can be calculated by an initial release amount for the first 24 hours. The initial release amount can be obtained from measuring AUC (Area Under the Concentration) of the blood concentration for 24 hours after subcutaneous administration of the sustained-release preparation of this invention; and applying the AUC value to standard calibration curve of the dose-AUC, which curve is obtained by subcutaneous administration of a physiologically active polypeptide solution.

The sustained-release preparation in the present invention can be used for preparing various dosage forms using the microcapsule as a source material, and is capable of administration as parenteral preparations (e.g., injections or preparations for implantation into muscle, hypodermis, tissues, etc., preparations for administering to mucosa onto cavitas nasi, rectum, uterus, etc.), oral preparations (e.g., capsules such as hard capsules and soft capsules, solid preparations such as granules and powders, solutions such as suspensions, etc.) and so on.

In particular, the sustained-release preparation in the present invention is preferably for injection. For example, in case that the sustained-release preparation is the microcapsule, it is possible to obtain the practical sustained-release preparation for injection by means of the aqueous suspension wherein the microcapsule is suspended together with dispersing agents (e.g., the surfactants such as Tween 80, HCO-60, etc., the polysaccharides such as carboxymethyl celluloses, sodium alginate, hyaluronic acid, etc.), preservatives (e.g., methylparaben, propylparaben, etc.), tonicity agents (e.g., sodium chloride, mannitol, sorbitol, glucose, etc.) and soon. It is also possible to obtain the practical sustained-release preparation for injection by means of an oily suspension wherein the microcapsule is suspended together with vegetable oil such as sesame oil, corn oil, a mixture thereof with a phospholipid such as lecithin, or medium-chain fatty acid triglycerides (e.g., Miglyol 812).

When the sustained-release preparation is, for example, a microcapsule, the particle size of the sustained-release preparation for an injectable suspension can be selected from the range satisfying the requirements for the degree of dispersion and the needle passability for the injection. For example, the particle size is within the range of about 0.1 to about 300 $\mu$m, preferably about 1 to about 150 $\mu$m, more preferably about 2 to about 100 $\mu$m, as the average particle size.

Methods of preparing the above microcapsule as a sterile preparation include, but are not limited to, the method in which the entire production process is sterile, the method in which the gamma rays are used as the sterilant, and the method in which an antiseptic is added during the manufacturing process.

The sustained-release preparation in the present invention can be safely used in mammals (e.g., humans, bovine, swine, dogs, cats, mice, rats, rabbits, etc.) with low toxicity.

Indication of the sustained-release preparation varies depending on the physiologically active polypeptide used. The sustained-release preparation is useful to prevent or treat diabetes when insulin is used as the physiologically active polypeptide; viral hepatitis (e.g., type C hepatitis, HBe antigen-positive active hepatitis, etc.) and cancer (e.g., renal carcinoma, multiple myeloma, etc.) when interferon-$\alpha$is used; anemia (e.g., anemia during dialysis of kidney, etc.) when erythropoietin is used; neutropenia (e.g., in cancer therapy, etc.) and infections when G-CSF is used; cancer (e.g., hemangioendothelioma, etc.) when IL-2 is used; fracture, wound (e.g., bedsore, etc.), periodontitis and gastrointestinal ulcer when FGF is used; thrombocytopenia when FGF-9 is used; senile dementia and neuropathy when NGF is used; thrombosis when TPA is used; and cancer when tumor necrosis factor is used. Further, the sustained-release preparation containing GH is applied to Turner's syndrome, chronic renal diseases, achondroplasia, and adult hypopituitarisin as well as pituitary dwarfism, based on growth hormone action of GH. Further, since, GH is reported to be applied to diseases such as Down syndrome, Silver syndrome, hypochondroplasia and juvenile chronic arthritis to provide excellent therapeutic effects, the sustained-release preparation containing GH can be applied to these diseases. The sustained-release preparation containing GH is also useful to prevent or treat congestive heartfailure, etc.

Although varying depending on the kinds and contents of the physiologically active polypeptide, duration of the release, target disease, subject animal species and other factors, the dose of the sustained-release preparation can be set at any level, as long as the effective concentration of the physiologically active polypeptide in the body is maintained. For example, when the sustained-release preparation is one designed for two week release, the dose of the physiologically active polypeptide can be suitably chosen from the range of preferably about 0.0001 to about 10 mg/kg body weight, more preferably about 0.05 to about 1 mg/kg body weight, per an adult. The preferred administration frequency of the sustained-release preparation can be suitably chosen from once a week, once every two weeks, once a month, once every two months and etc. depending on the kinds and contents of the physiologically active polypeptide, the dosage form, duration of the release, target disease, subject animal species and other factors. Preferably is the sustained-release preparation, which can effectively release a physiologically active polypeptide for a period ranging preferably from one week to one month, more preferably from one week to three weeks, further more preferably from 10 days to 20 days. Among those, the sustained-release preparation, which can effectively release a physiologically active polypeptide for a period of two weeks is the most preferable. It means the sustained-release preparation is administered once every two weeks.

When the physiologically active polypeptide as an active ingredient in the sustained-release preparation is, for example, insulin, the dose per administration to an diabetic adult is suitably chosen from the range of usually about 0.001 to about 1 mg/kg body weight, preferably about 0.01 to about 0.2 mg/kg body weight, as an effective ingredient. And the preferred administration frequency is once a week.

When the physiologically active polypeptide as an active ingredient in the sustained-release preparation is GH, the dose can be set at any level, as long as the effective concentration of GH in the body is maintained, although varying depending on the kinds and contents of GH, duration of the release, target disease, subject animal species and other factors. Regarding the treatment of the above described diseases, when the sustained-release preparation is one designed for two week release, the dose of GH can be suitably chosen from the range of about 0.01 to about 5 mg/kg body weight (about 0.03 to about 15 IU/mg/kg body weight), more preferably about 0.05 to about 1 mg/kg body weight(about 0.15 to about 3 IU/mg/kg body weight), per a child or an adult for safe administration. The preferred administration frequency can be suitably chosen from once a week, once every two weeks, once a month and etc., depending on. the contents of GH, the dosage form, duration of the release, target disease, subject animal species and other factors. Preferred is the sustained-release preparation containing GH, which can effectively release GH or a period ranging preferably from one week to one month, more preferably from one week to three weeks, further more preferably from 10 days to 20 days. Among those, the sustained-release preparation containing GH, which can effectively release GH for a period of two weeks is the most preferable. It means the sustained-release preparation is administered once every two weeks.

The sustained-release preparation is preferably stored at ordinary temperature or in a cold place. More preferably, the sustained-release preparation is stored in a cold place. The "ordinary temperature" and the "cold place" are defined in the pharmacopoeia of Japan. Namely, the "ordinary temperature" means 15 to 25° C., and the "cold place" means a temperature not exceeding 15° C. In the "cold place", it is more preferably about 2 to 8° C.

BEST MODE FOR CARRYING OUT THE INVENTION

The present invention is hereafter described in more detail by means of the following Reference Examples, Examples and Experimental Examples, which are not to be construed to limit the scope of the present invention. In the specification of the present invention, amino acid abbreviations are based on those recommended by the IUPAC-IUB Commission on Biochemical Nomenclature, or those used commonly in the related field. Examples are shown below (abbreviation represents L-type unless otherwise specified):

SDS: Sodium dodecylsulfate
Gly: Glycine
Ala: Alanine
Val: Valine
Leu: Leucine
Ile: Isoleucine
Ser: Serine
Thr: Threonine
Cys: Cystein
Met: Methionine
Glu: Glutamic acid
Gln: Glutamine
Asp: Aspartic acid
Asn: Asparagine
Lys: Lysine
Arg: Arginine
His: Histidine
Phe: Phenylalanine
Tyr: Tyrosine
Trp: Tryptophan
Pro: Proline
Asx: Asp+Asn
Glx: Glu+Gln Reference Example 1
Construction of Expression Vector for Human Growth Hormone (hGH) Using T7 Promoter The structure gene of hGH was isolated as about 0.75 kb fragment from plasmid pHGH107 (ATCC 31538 or ATCC 40011) described in Japanese Patent Publication Number 12996/1994 by means of cleavage with EcoRI and EcoRV. On the other hand, T7 promoter and ampicillin resistant gene were isolated as about 4.6 kb fragment from pET-3C, [Rosenberg et al., Gene, 56, 125 (1987)] by means of cleavage with NdeI and BamHI.

Both of the two fragments were treated with T4 DNA polymerase (DNA blunting kit; Takara Shuzo, Inc.) and ligated with T4 DNA ligase, followed by introduction into

*Escherichia coli* JM109 and selection of ampicillin resistant transformant. From the obtained 12 colonies, plasmids were prepared and digested with PstI. As a result, it was found that hGH gene was inserted in a correct direction in the plasmids from the 6 colonies. The plasmid obtained from one transformant among the 6 colonies was named as pTGA201.

Reference Example 2
Expression of Met-hGH in *Escherichia coli*

*Escherichia coli* JM109 was transformed with A phage (Studie, Supura) having RNA polymerase gene of T7 phage. Thereafter, into the obtained *Escherichia coli* JM109 (DE3), hGH expression vector pTGA201 obtained in Reference Example 1 was introduced to obtain *Escherichia coli* JM109 (DE3)/pTGA201.

*Escherichia coli* JM109 (DE3)/pTGA201 was inoculated into a 2 liter capacity flask containing 1 liter of LB medium [1% peptone, 0.5% yeast extract, 0.5% sodium chloride] comprising 50 µg/ml ampicillin and then subjected to rotary shaking cultivation at 30° C. for 16 hours. The resultant culture liquid was then transferred to a 50 liter jar fermentor containing 20 liter of LB medium [0.02% antiforming agent (New Pole LB-625; Sanyo Kasei Kogyo), 50 µg/ml ampicillin], after which it was subjected to cultivation under aeration and agitation at 37° C. for 6 hours The resultant culture liquid was then transferred to a 500 liter jar fermentor containing 360 liter of a liquid production medium (1.68% sodium hydrogen phosphate, 0.3% potassium dihydrogen phosphate, 0.1% ammonium chloride, 0.05% sodium chloride, 0.0246% magnesium sulfate, 0.02% New Pole LB-625, 0.0005% thiamine hydrochloride, 1.5% glucose, 1.5% casamino acid), after which it was subjected to cultivation under aeration and agitation at 37° C. When the Klett value was about 500, 5.95 mg/L/minute of isopropyl-β-D-thiogalactopyronoside (IPTG) was added to the medium and the cultivation was further continued for 4hours. The culture liquid was centrifuged to obtain about 4.5 kg of wet cells which were frozen at −8° C.

The above transformed *Escherichia coli* JM109 (DE3)/pTGA201 is on deposit with the National Institute of Bioscience and Human-Technology (NIBH), Agency of Industrial Science and Technology, Ministry of International Trade and Industry, Japan and has been assigned the Accession Number FERM BP-5632. It is also on deposit with the Institute for Fermentation, Osaka, Japan (IFO) and has been assigned the Accession Number IFO 16001.

Reference Example 3
Activation of Met-hGH

Two kg of wet cells obtained in Reference Example 2 was dissolved in 6 l of 50 mM Tris-HCl and guanidine hydrochloride (pH 8.0), followed by centrifugation (10000 rpm, 120 minutes). To 6 l of the resultant supernatant, was added 18 l of a solution (pH 8.0) containing 50 mM Tris-HCl, 0.28 mM GSSG and 0.7 M Arg to adjust pH 8.0, followed by standing at 4° C. for 5 days to continue activation of Met-hGH.

Reference Example 4
Purification of Met-hGH

The solution obtained in Reference Example 3 was subjected to salting-out and concentration by Pellicon cassette system (PTGC membrane; Millipore Corporation) with adding a solution (pH 8.0) of 20 mM Tris-HCl and 2.5 M urea until electric conduction became not more than 10 mS. The obtained concentrate was centrifuged (10000 rpm, 60 minutes) to obtain 5 l of supernatant. The supernatant was loaded on DEAE-Toyopearl 650M column (20 cmφ×84 cm, Tosoh) equilibrated with a solution (pH 8.0) of 20 mM Tris-HCl and 2.5Murea, followed by adsorption and washing. The column was eluted using a concentration gradient consisting of 0–25% solution B (B=20 mM Tris-HCl, 2.5 M urea, 1M NaCl, pH 8.0) at 300 ml/minute of flow rate for 100 minutes. The eluted solution 10 1 containing Met-hGH was again subjected to salting-out and concentration by Pellicon cassette system (PTGC membrane; Millipore). The concentrated solution was passed through DEAE-5PW column (21 cmφ×30 cm, Tosoh) using HPLC method (Gilson HPLC system; Gilson). The column was eluted using a pH gradient consisting of 70–85% solution B (A=50 mM Tris-HCl and 2.5 M urea (pH 8.0); B=50 MM MES [2-(N-morpholino)ethane sulfonate] and 2.5 M urea (pH 4.0)) at 320 ml/minute of flow rate for 70 minutes. To the obtained Met-hGH fraction 6 1, was added 2 M Tris-HCl (pH 7.8) to adjust pH 7.2, followed by salting-out and concentration by Pellicon cassette system (PTGC membrane; Millipore) to obtain 9,979 mg of Met-hGH.

Reference Example 5
Removal of N-terminal Met

To 1650 ml solution of Met-hGH obtained in Reference Example 4, was added 413 ml solution containing 35 mM copper sulfate, 2.5 M glyoxylic acid and 6 M pyridine and the mixture was stirred and allowed to stand at 25° C. for 60 minutes. The reaction solution was passed at 3 1/h of flow rate through Sephadex G-25 column (11.3 cm φ×125 cm, Pharmacia) equilibrated with a solution (pH 8.0) of 20 mM Tris-HCl and 2.5 M urea and the column washed with the same solution to collect the fraction of diketone derivative of Met-hGH. The eluted fraction was directly added to 4 l solution of 4M acetic acid, 4 M sodium acetate, 80 mM o-phenylenediamine and 3 M urea with stirring. After the elution, the reaction solution 8 l was allowed to stand at 4° C. for 3 days. The solution was subjected to salting-out by Pellicon cassette system (PTGC membrane; Millipore). The concentrated solution 4 l was passed at 3 /l h of flow rate through Sephadex G-25 column (11.3 cmφ×140 cm, Pharmacia) equilibrated with a solution (pH 8.0) of 20 mM Tris-HCl and 2.5 M urea to collect the fraction 4.71of hGH. The obtained fraction was passed through DEAE-5PW column (21 cmφ×30 cm, Tosoh) using HPLC method (Gilson HPLC system; Gilson). The column was eluted with using a pH gradient consisting of 70 to 85% solution B (A=50 mM Tris-HCl and 2.5 M urea (pH 8.0); B=50 mM MES [2-(N-morpholino)ethane sulfonate] and 2.5 M urea (pH 4.0)) at 320 ml/minute of flow rate for 70 minutes to collect 10 1 fraction of hGH. To the obtained hGH fraction, was added 500 ml solution of 2 M Tris-HCl (pH 7.8) to adjust pH 7.2, followed by concentration with Minitan II (PTGC membrane; Millipore). The concentrated solution 500 ml was passed at 2/l h of flow rate through Sephacryl S-100 column (11.3 cmφ×50 cm, Pharmacia) equilibrated with distilled water to collect the hGH fraction 1651 ml, followed by filtration with Millipack 60 (Millipore) to obtain hGH solution 1487 ml (3309 mg of hGH).

Reference Example 6
Confirmation of ° Feature of hGH (a) Analysis with SDS-polyacrylamide Gel Electrophoresis To the hGH solution obtained in Reference Example 5 was added the same volume of Sample buffer [Laemmli, Nature, 227, 680 (1970)] containing 100 mM DTT, and the mixture was heated at 95° C. for 2 minutes, followed by electrophoresis with Multi Gel 10/20 (Daiichi Pure Chemicals). After electrophoresis, the gel was stained with Coomassie brilliant blue and only one single band at about 22, kd of the purified protein was obtained. Therefore, it was confirmed that the hGH was almost pure.

(b) Analysis of Amino Acid Composition

The hGH obtained in Reference Example 5 was used for the determination of amino acid composition with amino acid analyzer (L-8500A, Hitachi). The amino acid composition of hGH obtained in Reference Example 5 agreed with that predicted from cDNA sequence of hGH. The results are shown in Table 1.

TABLE 1

Analysis of amino acid composition

| Amino acid | Number of residues per 1 mole | Values predicted from cDNA sequence of hGH |
|---|---|---|
| Asx | 20.2 | 20 |
| Thr[1] | 10.0 | 10 |
| Ser[1] | 16.7 | 18 |
| Glx | 27.0 | 27 |
| Pro | 8.1 | 8 |
| Gly | 8.2 | 8 |
| Ala | 7.6 | 7 |
| Cys | N.D.[2] | 4 |
| Val | 7.0 | 7 |
| Met | 3.0 | 3 |
| Ile | 7.7 | 8 |
| Leu | 27.9 | 26 |
| Tyr | 8.1 | 8 |
| Phe | 12.7 | 13 |
| His | 3.2 | 3 |
| Lys | 8.9 | 9 |
| Arg | 10.9 | 11 |
| Trp | 0.8 | 1 |

Acid hydrolysis (6N HCl, 4% thioglycolic acid, 110° C., Mean value of those obtained after 24 and 48 hours of hydrolysis)
[1]Value extrapolated on the assumption that hydrolysis time was 0 hours.
[2]Undetected Analysis was carried out using 20 A g of hGH.

(c) Analysis of N-terminal Amino Acid Sequence

The N-terminal amino acid sequence of hGH obtained in Reference Example 5 was determined using a gas-phase protein sequencer (Applied Biosystems, 477A model). The N-terminal amino acid sequence of hGH obtained in Reference Example 5 agreed with that predicted from cDNA sequence of hGH. The results are shown in Table 2.

TABLE 2

Analysis of N-terminal amino acid sequence

| Residue No. | PTH[1]-amino acid detected (pmol) | amino acid predicted from cDNA sequence of hGH |
|---|---|---|
| 1 | Phe (949) | Phe |
| 2 | Pro (404) | Pro |
| 3 | Thr (422) | Thr |
| 4 | Ile (744) | Ile |
| 5 | Pro (283) | Pro |
| 6 | Leu (514) | Leu |
| 7 | Ser (136) | Ser |
| 8 | Arg (36) | Arg |
| 9 | Leu (377) | Leu |
| 10 | Phe (408) | Phe |
| 11 | Asp (77) | Asp |
| 12 | Asn (230) | Asn |
| 13 | Ala (435) | Ala |
| 14 | Met (334) | Met |
| 15 | Leu (398) | Leu |
| 16 | Arg (67) | Arg |
| 17 | Ala (488) | Ala |
| 18 | His (30) | His |

TABLE 2-continued

Analysis of N-terminal amino acid sequence

| Residue No. | PTH[1]-amino acid detected (pmol) | amino acid predicted from cDNA sequence of hGH |
|---|---|---|
| 19 | Arg (42) | Arg |
| 20 | Leu (406) | Leu |

[1]phenylthiohydantoin

Analysis was carried out using 1 nmol of hGH.

(d) Analysis of C-terminal Amino Acid

The hGH obtained in Reference Example 5 was used for the determination of C-terminal amino acid with amino acid analyzer (L-8500A, Hitachi). The C-terminal amino acid of hGH obtained in Reference Example 5 agreed with that predicted from cDNA sequence of hGH. The results are shown in Table 3.

TABLE 3

(d) Analysis of C-terminal amino acid

| C-terminal amino acid | Yield (%) |
|---|---|
| Phe | 52 |

Vapor-phase hydrazinolysis (100° C., 6 hours)

Analysis was carried out using 18nmol of hGH.

(e) Determination of hGH Activity

Assay of hGH purified and obtained in Reference Example 5 was carried out using Nb 2 cells according to the method described, in Journal of Clinical Endocrinology and Metabolism, 51, 1058 (1980) and revealed that hGH purified and obtained in Reference Example 5 had a cell growth enhancing activity substantially identical to a standard product.

EXAMPLE 1

(1) Production of hGH Powder

Ethanol was added into the aqueous solution of a recombinant hGH (final concentration of hGH=2 mg/ml) prepared according to Reference Example 5 [final concentration (V/V%)=0.03%, 0.06%, 0.1%, 0.15%, 0.25%, 0.5%)]. Then, the resulting solution was lyophilized to obtain 6 kinds of the hGH powder.

(2) Production, of a Microcapsule Including hGH 1.85 g of the lactic acid/glycolic acid copolymer (lactic acid/glycol=50/50, average molecular weight as a converted value to polystyrene=12,000, viscosity=0.145 dl/g) and 10 mg of zinc oxide were dissolved in 3.0 ml of dichloromethane. 140 mg of the hGH powder prepared in the above (1) was added into the above organic solvent solution. Then, it was atomized by using Polytron (commercially available from Kinematica). The S/O dispersion was added into 800 ml of aqueous solution of 0.1% polyvinyl alcohol. Then, the resulting liquid was stirred and emulsified using a homomixer. Dichloromethane was evaporated with stirring for 3 hours at the room temperature and then the dispersion was centrifuged (about 1,500 rpm) to collect a microcapsule. Subsequently, the microcapsule was washed 2 times with 400 ml of distilled water, added 0.2 g of D-mannitol and then lyophilized. Further, the resulting substance was dried in vacuo at 46° C. for 3 days for removing the remaining solvent to obtain 6 kinds of the microcapsule including hGH.

EXAMPLE 2

(1) Production of hGH Powder 10,20,25,40,50, 70and 100 times of mole equivalent of ammonium acetate was added into the aqueous solution of the recombinant hGH (final concentration of hGH=2 mg/ml) prepared according to Reference Example 5. Then, the resulting liquid was lyophilized to obtain 7 kinds of the hGH powder.

(2) Production of a Microcapsule Including hGH

According to the process as described in the above Example 1 (2), 7 kinds of the microcapsule including hGH were obtained by using the hGH powder prepared in the above (1).

Comparative Example 1

(1) Production of hGH Powder

Neither ethanol nor ammonium acetate was added into the aqueous solution of the recombinant hGH (final concentration of hGH=2 mg/ml) prepared according to Reference Example 5. The solution was lyophilized to obtain the hGH powder.

(2) Production of a Microcapsule Including hGH

According to the process as described in the above Example 1 (2), the microcapsule including hGH was obtained by using the hGH powder prepared in the above (1).

Experimental Example 1

As to the hGH powder obtained in Example 1 (1) and Comparative Example 1 (1), the ease of handling was evaluated from a point of view of volume of powder and charge against static electricity. The results are shown in Table 4.

As obviously understood from the results of Table 4, in comparison with the hGH powder prepared without ethanol, the hGH powder prepared with ethanol was extremely improved as to ease of handling.

Experimental Example 2

2 ml of dichloromethane was added into 50 μl of the S/O dispersion which is the hGH powder/PLGA organic solvent obtained in the middle of the process of Example 1 (2) and Comparative Example 1 (2). Then, average particle size of the hGH powder was measured by using a laser diffraction particle size analyzer (commercially available under the name of SALD2000A from Shimadzu Corp.). The results are shown in Table 4.

As obviously understood from the results of Table 4, while the hGH powder prepared without ethanol had the average particle size which was not less than 10 μm, the hGH powder prepared with ethanol had the average particle size which was not more than 10 μm.

TABLE 4

| Concentration of ethanol | Easiness of handling* | Average particle size |
| --- | --- | --- |
| 0.03% | + | 8.2 μm |
| 0.06% | ++ | 5.6 μm |
| 0.10% | ++ | 5.0 μm |
| 0.15% | ++ | 6.1 μm |
| 0.25% | ++ | 8.0 μm |

TABLE 4-continued

| Concentration of ethanol | Easiness of handling* | Average particle size |
| --- | --- | --- |
| 0.50% | ++ | 9.1 μm |
| Without ethanol | − | 10.2 μm |

*Evaluated in the 3 grades from a point of view of volume of powder and charge against static electricity (−: difficult, +: easy, ++: extremely easy)

Experimental Example 3

The following tests were performed by using the microcapsule including hGH produced in Example 1 (2) and Comparative Example 1 (2).

(1) hGH Content.

0.3 ml of acetonitrile was added to 5 mg of the microcapsule, and the mixture was subjected to ultrasonication. 0.7 ml of 10 mM phosphate buffered saline (pH 8.0) was added to the resultant solution to extract hGH which is the active component. Subsequently, the hGH extract was subjected to the size exclusion high-performance liquid chromatography in the following condition, and then hGH content was measured to calculate the entrapment ratio. The results are shown in Table 5.

Column: TSKgelG 3000SW$_{XL}$ (commercially available from Tosoh)

Extract: 0.2 M phosphate buffered saline (pH 6.8)—0. 2 M NaC

Flow rate: 0.6 ml/min

As obviously understood from the results of Table 5, in comparison with the microcapsule (including hGH) produced by using the hGH powder prepared without ethanol, the microcapsule including hGH produced by using the hGH powder prepared with ethanol showed higher hGH entrapment ratio.

TABLE 5

| Concentration of ethanol | hGH entrapment ratio |
| --- | --- |
| 0.10% | 92% |
| 0.25% | 90% |
| 0.50% | 85% |
| Without ethanol | 77% |

(2) In Vivo Release Profile

The microcapsule was subcutaneously administered (6 mg as amount of hGH/rat) to the immuno-suppressed SD rats (male, aged 6 weeks). Then, rat blood was serially collected as time passed. The concentration of hGH in serum was measured by the radioimmunoassay (commercially available under the name of Ab beads HGH from EIKEN CHEMICAL CO., LTD.) to evaluate the hGH release profile. The immuno-suppressed SD rat was prepared by subcutaneous injection of Prograf® (commercially available from Fujisawa Pharmaceutical Co., Ltd.) in the amounts of 0.4 mg/rat 3 days before the first administration of the microcapsule, of 0.2 mg/rat at the time of the first administration, and of 0.2 mg/rat on 4th day, 7th day, 11th day and 14th day after the first administration. The results are shown in FIG. 1.

Figure 1:
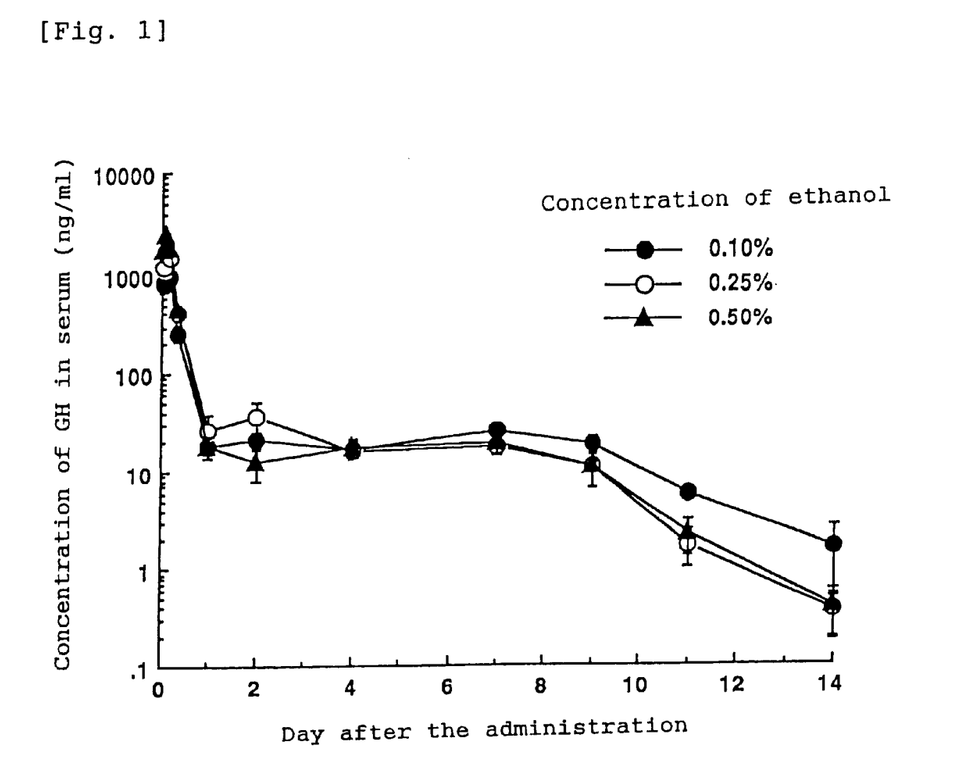
FIG. 1 shows the change of GH concentration in serum after the microcapsule including GH obtained by using the GH powder added ethanol is administered to the immune suppressed SD rat, wherein -●-shows 0.10% ethanol, -○-shows 0.25% ethanol, -▲-shows 0.50% ethanol.

As obviously understood from the results of FIG. 1, as to the microcapsule (including hGH) produced by using the hGH powder prepared with ethanol, the initial release (which is amount of released hGH for 1 day (24 hours) after the administration) was low, but continuing concentration (in other words, amount of released hGH for 2 weeks after the administration excepting the initial release) was high. In other words, by means of the hGH powder prepared with ethanol, the initial release was reduced, and high concentration of hGH in blood for 2 weeks was accomplished.

Experimental Example 4

As to the hGH powder obtained in Example 2 (1) and Comparative Example 1 (1), the easiness of handling was evaluated from a point of view of volume of powder and charge against static electricity. The results are shown in Table 6.

As obviously understood from the results of Table 6, in comparison with the hGH powder prepared without ammonium acetate, the hGH powder prepared with ammonium acetate was extremely improved as to the easiness of handling.

Experimental Example 5

According to the process as described in the above Experimental Example 2, the S/O dispersion which is the hGH powder/PLGA organic solvent obtained in the middle of the process of Example 2 (2) and Comparative Example 1 (2) was subjected to a laser diffraction particle size analyzer (commercially available under the name of SALD2000A from Shimadzu Corp.) to measure average particle size of the hGH powder. The results are shown in Table 6.

TABLE 6

| Amount of added ammonium acetate | Easiness of handling* | Average particle size |
|---|---|---|
| 10 times mole | + | 2.8 μm |
| 20 times mole | ++ | 3.0 μm |
| 25 times mole | ++ | 4.1 μm |
| 40 times mole | ++ | 4.2 μm |
| 50 times mole | ++ | 4.0 μm |
| 70 times mole | ++ | 7.2 μm |
| 100 times mole | − | 11.8 μm |
| Without ammonium acetate | − | 10.2 μm |

*Evaluated in the 3 grades from a point of view of volume of powder and charge against static electricity (−: difficult, +: easy, ++: extremely easy)

Experimental Example 6

The following tests were performed by using the microcapsule including hGH produced in Example 2 (2) and Comparative Example 1 (2).

(1) hGH Content

According to the process as described in the above Experimental Example 1 (1), hGH entrapment ratio of each microcapsule was evaluated. The results are shown in Table 7.

As obviously understood from the results of Table 7, in comparison with the microcapsule (including hGH) produced by using the hGH powder prepared without ammonium acetate, the microcapsule (including hGH) produced by using the hGH powder prepared with ammonium acetate showed higher hGH entrapment ratio.

(2) Initial Release

According to a method mentioned below, the initial release ratios of the microcapsules were calculated. These results are shown in Table 7 as well.

The aqueous solutions of hGH (concentration: 5, 10, 20 mg/kg) were subcutaneously administered to the immuno-suppressed SD rats (male, aged 6 weeks). Then, rat blood was serially collected as time passed up to 24 hours after the administration. In solution, the concentrations of hGH in serum of the rat blood were measured by radio-immunoassay (Ab beads HGH: Eiken Kagaku Co.). A calibration curve of administration dose and AUC was obtained based on the resulted AUC value of the each aqueous solution.

The microcapsule was subcutaneously administered (6 mg as amount of hGH/rat) to the immuno-suppressed SD rats (male, aged 6 weeks). Then, rat blood was serially collected as time passed up to 24 hours after administration. The concentration of hGH in serum was measured by the radioimmunoassay (commercially available under the name of Ab beads HGH from EIKEN CHEMICAL CO., LTD.) to evaluate the hGH release profile. The resulted AUC value was applied to the above calibration curve of administration dose and AUC to obtain an initial release amount of hGH, and then, an initial release ratio was calculated therefrom.

TABLE 7

| Amount of added ammonium acetate | hGH entrapment ratio | Initial release ratio |
|---|---|---|
| 10 times mole | 100% | 11.0% |
| 20 times mole | 92% | 11.8% |
| 25 times mole | 95% | 19.8% |
| 40 times mole | 85% | 20.0% |
| 50 times mole | 83% | 23.3% |
| 70 times mole | 82% | 29.5% |
| 100 times mole | 70% | 48.7% |
| Without ammonium acetate | 77% | 41.7% |

(3) In vivo Release Profile

According to the process as described in the above Experimental Example 1 (2), the hGH release profile of the microcapsule was evaluated by using the immuno-suppressed SD rats. The results are shown in FIG. 2.

Figure 2:
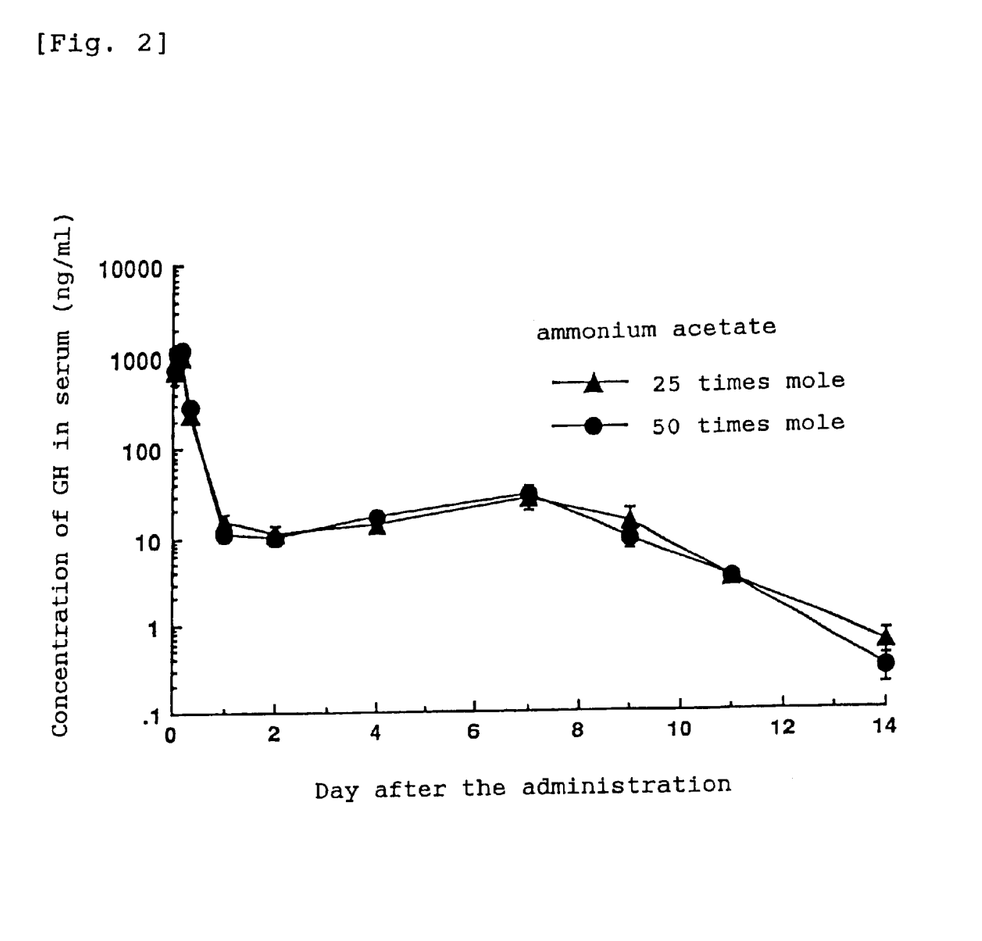
FIG. 2 is a graph which shows the change of GH concentration in serum after the microcapsule including GH obtained by using the GH powder added ammonium acetate is administered to the immune suppressed SD rat, wherein -▲-shows 25 times mole of ammonium acetate, -●-shows 50 times mole of ammonium acetate.

As obviously understood from the results of FIG. 2, as to the microcapsule (including hGH) produced by using the hGH powder prepared with ammonium acetate, the initial release (which is amount of released hGH for 1 day (24 hours) after the administration) was low, but continuing concentration (in other words, amount of released hGH for 2 weeks after the administration excepting the initial release) was high. In other words, by means of the hGH powder prepared with ammonium acetate, the initial release was reduced and high concentration of hGH in blood for 2 weeks was accomplished.

Industrial Applicability

In accordance with the present invention, the ease of handling of the physiologically active polypeptide powder is improved in the process for producing the preparation, and it is possible to industrially produce the sustained-release preparation on a large scale. Further, there is provided a sustained-release preparation, which shows high and stable concentration of the active component in blood in long term, and low initial release ratio of the physiologically active polypeptide. The present method heightens the entrapment ratio of the physiologically active polypeptide into the sustained-release preparation.

What is claimed is:

1. A method for producing a sustained-release preparation of a growth hormone comprising the steps of:

a) adding a volatile salt to an aqueous solution of a growth hormone to form a product solution;

b) lyophilizing said product solution of step a) to form a powder comprising particles;

c) dispersing said powder of step b) into an organic solvent solution of a biodegradable polymer to form a dispersion; and d) removing said organic solvent from said dispersion of step c) to obtain a sustained release preparation of a growth hormone.

2. The method according to claim 1, wherein the average particle size of said particles of step b) is not more than 10 μm in diameter.

3. The method according to claim 1, wherein said growth hormone is human growth hormone.

4. The method according to claim 1 further comprising adding an alcohol to said aqueous solution of said growth hormone in step a).

5. The method according to claim 4, wherein the alcohol is methanol or ethanol.

6. The method according to claim 4, wherein the alcohol is ethanol.

7. The method according to claim 1, wherein the volatile salt is an ammonium salt.

8. The method according to claim 7, wherein the ammonium salt is ammonium acetate, ammonium bicarbonate or ammonium carbonate.

9. The method according to claim 7, wherein the ammonium salt is ammonium acetate.

10. The method according to claim 7, wherein the molar ratio of said ammonium salt relative to said growth hormone is from about 10:1 to about 80:1.

11. The method according to claim 1, wherein the biodegradable polymer is lactic acid/glycolic acid polymer.

12. The method according to claim 11, wherein said biodegradable polymer has a ratio of lactic acid to glycolic acid of from about 100:0 to about 40:60.

13. The method according to claim 11, wherein the biodegradable polymer comprises lactic acid/glycolic acid polymer having a weight-average molecular weight of about 3,000 to about 50,000.

14. The method according to claim 11, wherein the lactic acid/glycolic acid polymer is in a form of a polyvalent metal salt.

15. The method according to claim 14, wherein the polyvalent metal is zinc.

16. The method according to claim 1 further comprising micro-encapsulating said sustained-release preparation obtained in step d) to form microcapsules.

17. The method according to claim 16, wherein the average particle size of said microcapsules is from about 0.1 μm to about 300 μm.

18. The method according to claim 1, wherein the resulting sustained-release preparation is suitable for administration by injection.

19. A sustained-release preparation produced by the method according to claim 1.

20. A method for producing a growth hormone powder comprising the steps of:

a) adding a volatile salt or a volatile salt and a water-miscible organic solvent into an aqueous solution of a growth hormone to form a product solution; and then b) lyophilizing said product solution of step a) to form a powder comprising particles wherein the average size of said particles is not more than about 10 μm.

21. A growth hormone powder which is obtained by the method according to claim 20.

22. A method of using said sustained release preparation of claim 1 for the manufacture of a medicament, said method comprising combining said sustained release preparation of claim 1 with a pharmaceutically acceptable carrier, diluent or excipient.

* * * * *